(12) United States Patent
Awad et al.

(10) Patent No.: US 9,428,399 B1
(45) Date of Patent: Aug. 30, 2016

(54) SYNTHESIS OF NANOPARTICLES OF METALS AND METAL OXIDES USING PLANT SEED EXTRACT

(71) Applicant: KING SAUD UNIVERSITY, Riyadh (SA)

(72) Inventors: Manal Ahmed Gasmelseed Awad, Riyadh (SA); Awatif Ahmed Hendi, Riyadh (SA); Mai Abdelrahman Elobeid Wagealla, Riyadh (SA); Khalid Mustafa Osman Ortashi, Riyadh (SA); Promy Virk, Riyadh (SA)

(73) Assignee: KNG SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/868,358

(22) Filed: Sep. 28, 2015

(51) Int. Cl.
| | |
|---|---|
| *C01G 9/02* | (2006.01) |
| *A61K 33/30* | (2006.01) |
| *A61K 33/38* | (2006.01) |
| *A61K 33/24* | (2006.01) |
| *C02F 1/72* | (2006.01) |
| *B22F 9/24* | (2006.01) |
| *B22F 1/00* | (2006.01) |
| *C22B 7/00* | (2006.01) |
| *C22B 3/00* | (2006.01) |
| *C22B 19/20* | (2006.01) |
| *C22B 19/34* | (2006.01) |
| *C02F 101/10* | (2006.01) |
| *C02F 101/12* | (2006.01) |

(52) U.S. Cl.
CPC .............. *C01G 9/02* (2013.01); *A61K 33/24* (2013.01); *A61K 33/30* (2013.01); *A61K 33/38* (2013.01); *B22F 1/0018* (2013.01); *B22F 1/0044* (2013.01); *B22F 9/24* (2013.01); *C02F 1/725* (2013.01); *C22B 7/006* (2013.01); *C22B 11/042* (2013.01); *C22B 19/20* (2013.01); *C22B 19/34* (2013.01); *C02F 2101/10* (2013.01); *C02F 2101/101* (2013.01); *C02F 2101/12* (2013.01); *C02F 2303/04* (2013.01); *Y10S 977/773* (2013.01)

(58) Field of Classification Search
None
See application file for complete search history.

(56) References Cited

U.S. PATENT DOCUMENTS

| 8,057,682 B2 | 11/2011 | Hoag et al. | |
|---|---|---|---|
| 9,144,544 B1 * | 9/2015 | Alsalhi | A61K 9/148 |
| 2011/0110723 A1 | 5/2011 | Varma et al. | |

OTHER PUBLICATIONS

SA Aromal. D Philip. "Green synthesis of gold nanoparticles using Trigonella foenum-graecum and its size-dependent catalytic activity." Spectrochimica Acta Part A: Molecular and Biomolecular Spectroscopy. vol. 97, 2012, pp. 1-5.*
AK Mittal, Y Chisti, UC Banerjee. "Synthesis of metallic nanoparticles using plant extracts." Biotechnology Advances, vol. 31, 2013, pp. 346-356.*
K Vishwakarma. "Green Synthesis of ZnO Nanoparticles Using Abrus precatorius Seeds Extract and Their Characterization." M.Sc Thesis, National Institute of Technology Rourkela. Dec. 5, 2013. pp. 11 initial pages and pp. 1-41 (52 total sheets).*
SM Berge, LD Bighley, DC Monkhouse. "Pharmaceutical Salts." Journal of Pharmaceutical Sciences, vol. 66 No. 1, Jan. 1977, pp. 1-19.*

* cited by examiner

*Primary Examiner* — Isaac Shomer
(74) *Attorney, Agent, or Firm* — Richard C. Litman (57) ABSTRACT

The synthesis of nanoparticles of metals and metal oxides using plant seeds extract involves providing a solution comprising a metal ion; providing a plant seeds extract solution that comprises a reducing agent; and combining the metal ion solution and the plant extract solution while stirring at room temperature to produce metal nanoparticles. The plant extract is obtained from *Trigonella foenum-graecum* seeds, and the metal ion is selected from the group consisting of silver (Ag), gold (Au) and zinc (Zn).

5 Claims, 11 Drawing Sheets

SYNTHESIS OF NANOPARTICLES OF METALS AND METAL OXIDES USING PLANT SEED EXTRACT

BACKGROUND OF THE INVENTION

1. Field of the Invention

The present invention relates to nano-biotechnology, and particularly to the synthesis of nanoparticles of metals and metal oxides using plant seeds extract, and to the use of these nanoparticles in treatment of sewage water and as antibacterial agents.

2. Description of the Related Art

Nano-biotechnology represents the intersection of nanotechnology and biotechnology, which is an emerging field dedicated to the creation and utility of nanoscale structures. An important area of research and development in this field is the synthesis of nanoparticles. Metal nanoparticles are especially of great interest owing to their distinctive features, such as catalytic, optical, magnetic and electrical properties. Nanoparticles exhibit completely new or improved properties compared to the bulk materials, and these properties are derived from the variation in size, morphology and distribution of the particles. The biosynthesis of noble metal nanoparticles (e.g., silver and gold) has received considerable attention due to their wide application in consumer products, medicine, pharmaceutical and other biomedical products.

Various mechanical, chemical and biological methods have been employed to synthesize nanomaterials. Examples of mechanical processes for producing nanoparticles include mechanical attrition (e.g., ball milling), crushing of sponge iron powder, and thermal quenching. Examples of chemical processes for producing nanoparticles include precipitation techniques, sol-gel processes, and inverse-micelle methods. Chemical synthesis methods (such as sol-gel process, micelle, chemical precipitation, hydrothermal method, pyrolysis, chemical vapor deposition etc.), however, lead to the presence of some toxic chemical species adsorbed on the surface that may have adverse effects in medical applications. Some reactions require high temperature and/or high pressure for initiating the reaction, while other reactions require inert atmosphere protection, and/or require noxious $H_2S$ gas, toxic template and stabilizers. Thus, chemical methods used for synthesis and stabilization of nanoparticles lead to non-ecofriendly byproducts.

On the other hand, biological approaches using microorganisms and plants or plant's extracts for synthesis of metal nanoparticles have been suggested as viable alternatives to chemical methods. Several biological systems including bacteria, fungi and yeast have been used in the synthesis of nanoparticles. Synthesis of nanoparticles using microorganisms, however, involves an elaborate process of maintaining cell cultures, intracellular synthesis and multiple purification steps. In this regard, using "green" methods in the synthesis of metal nanoparticles has received attention as conventional chemical methods are expensive and require the use of hazardous chemical compounds and organic solvents.

Thus, the synthesis of nanoparticles of metals and metal oxides using plant seeds extract solving the aforementioned problems is desired.

SUMMARY OF THE INVENTION

The synthesis of nanoparticles of metals and metal oxides using plant seeds extract involves providing a solution comprising a metal ion; providing a plant seeds extract solution that comprises a reducing agent; and combining the metal ion solution and the plant extract solution while stirring at room temperature to produce metal nanoparticles. The plant extract is obtained from *Trigonella foenum-graecum* seeds, and the metal ion is selected from the group consisting of silver (Ag), gold (Au) and zinc (Zn).

The nanoparticles may be used for reducing the concentration of a contaminant in sewage water by a method that comprises combining a metal or metal oxide nanoparticle (Ag, Au or ZnO) produced using the plant seeds extract with the sewage water; and allowing the metal or metal oxide nanoparticle to reduce the concentration of the contaminant, wherein the contaminant is selected from the group consisting of bacteria, sulfate ions, chloride ion, bicarbonate ion, magnesium ion, calcium ion and combinations thereof.

The nanoparticles may also be used for inhibiting bacterial growth on a wound or burn area by a method that comprises administering the metal or metal oxide nanoparticles to the wound or burn area to inhibit the growth of bacteria.

These and other features of the present invention will become readily apparent upon further review of the following specification and drawings.

DETAILED DESCRIPTION OF THE PREFERRED EMBODIMENTS

The synthesis of nanoparticles of metals and metal oxide using plant seeds extract involves providing a solution comprising a metal ion; providing a plant seeds extract solution that comprises a reducing agent; and combining the metal ion solution and the plant extract solution while stirring at room temperature to produce metal nanoparticles. The plant extract is obtained from *Trigonella foenum-graecum* seeds, and the metal ion is selected from the group consisting of silver (Ag), gold (Au) and zinc (Zn). In particular, the aqueous seeds extract of *Trigonella foenum-graecum* is used as a reducing agent to produce the metal (or metal oxide) nanoparticles. As used herein, the term "seeds extract" encompasses, for example, any chemical or combination of chemicals found in the seeds of the plant, including the derivatives of the compounds found in the seeds via chemical reaction. The "seeds extract" can be obtained from the plant by any process, for example, cold water extraction, hot water extraction, extraction with an organic solvent, and/or extraction with a supercritical solvent. The synthesis includes green and sustainable pathways that reduce or eliminate waste generation, use environmentally friendly solvents, and/or use environmentally friendly reducing agents. The following examples will further illustrate the synthesis process.

Example 1

Green Synthesis of Silver (Ag) Nanoparticles

Figure 1:
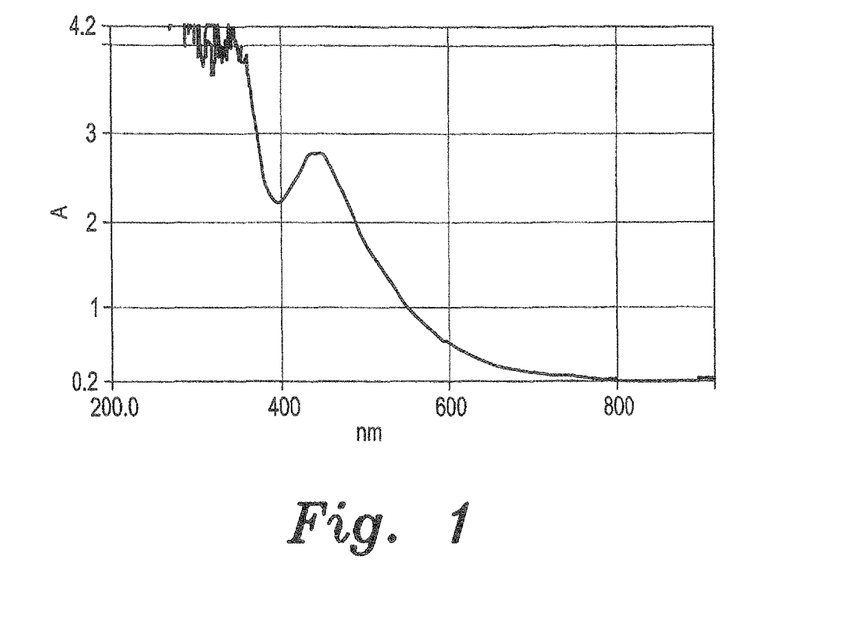
FIG. 1 is the UV-Vis spectrum of silver (Ag) nanoparticles synthesized using plant seeds extract according to the present invention.
Figure 2:
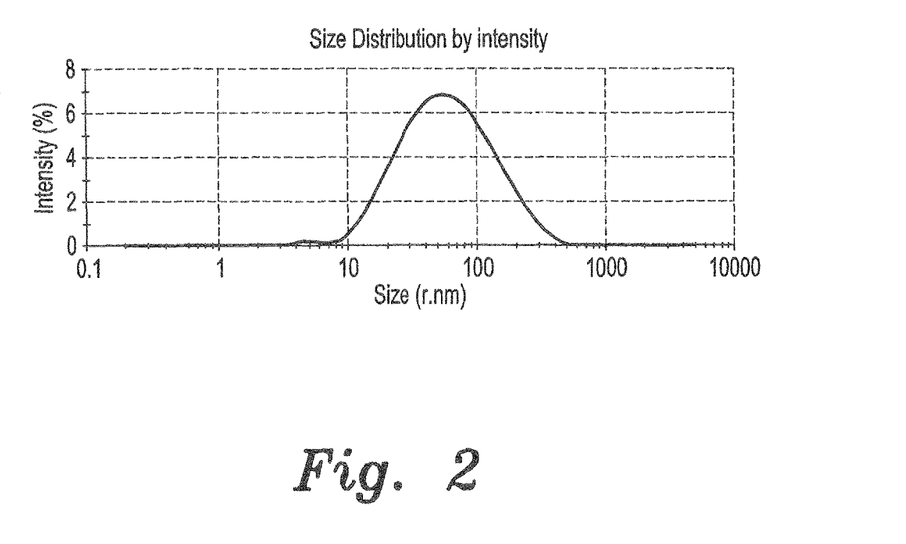
FIG. 2 is a chart showing the size distribution of silver (Ag) nanoparticles synthesized using plant seeds extract according to the present invention as obtained by a Zita sizer.
Figure 3A:
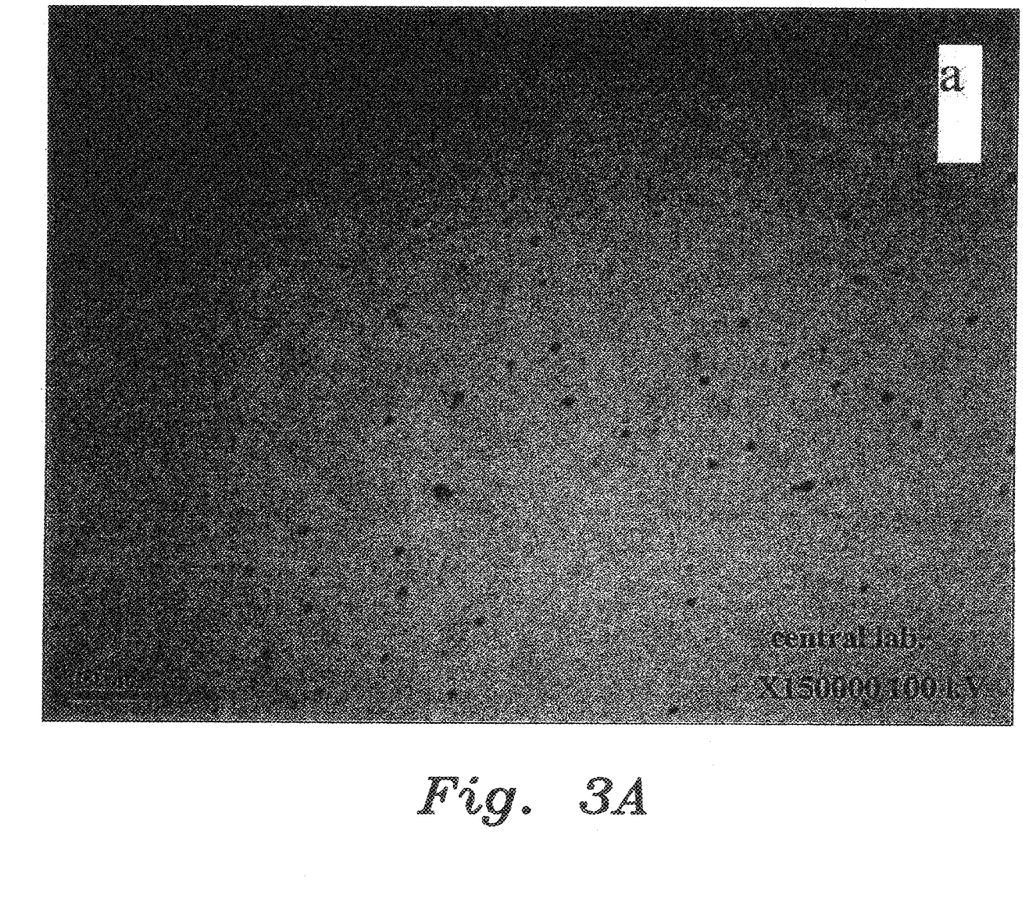
FIG. 3A is a Transmission Electron Microscopy (TEM) micrograph of silver (Ag) nanoparticles synthesized using plant seeds extract according to the present invention at 150000× magnification.
Figure 3B:
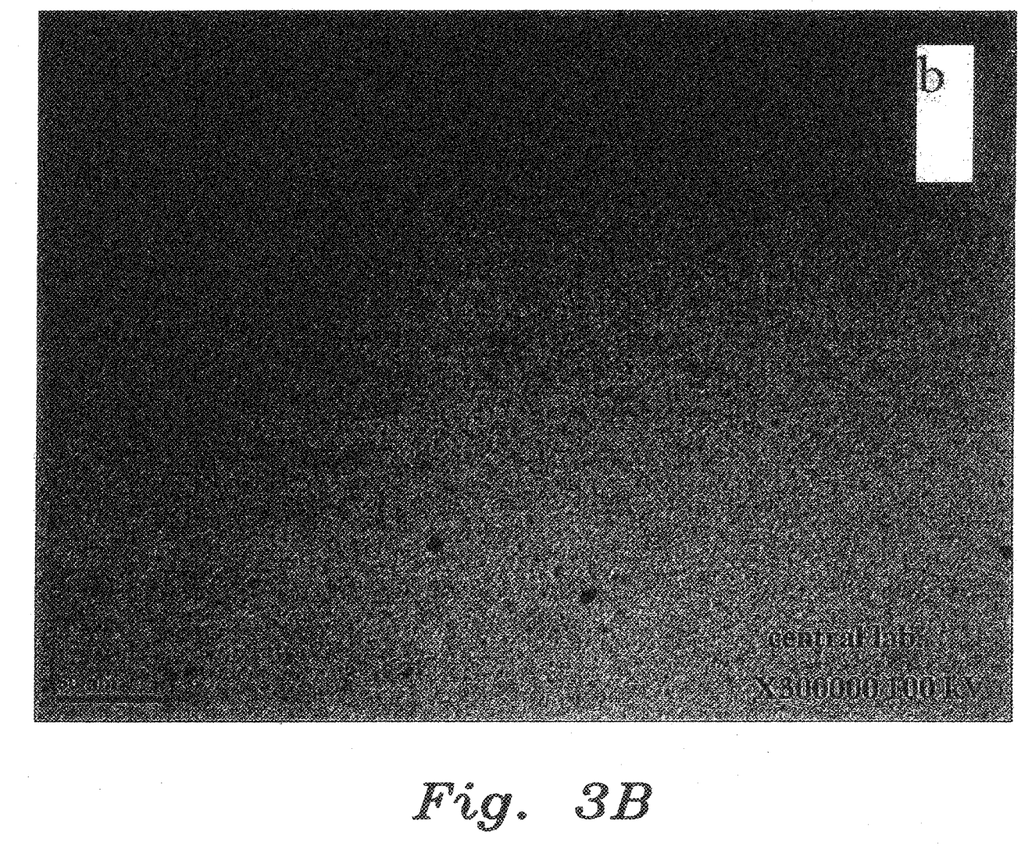
FIG. 3B is a Transmission Electron Microscopy (TEM) micrograph of silver (Ag) nanoparticles synthesized using plant seeds extract according to the present invention at 300000× magnification.

Silver nanoparticles were prepared according to the following method. About 15 mg of the seeds of the plant (*Trigonella foenum-graecum*) was soaked in about 30 ml of distilled water overnight, then filtered, and the aqueous extract was set aside until used. About 5 ml of the extract was added to about 50 ml of an aqueous solution of 0.001 mole/L silver nitrate ($AgNO_3$) and stirred for about 15 minutes at 45° C. Reduction of the silver ions by the seeds extract of *Trigonella foenum-graecum* resulted in the formation of silver nanoparticles. This reduction process was monitored by the change of color from colorless to dark brown. FIG. 1 shows the absorption peak of the silver nanoparticles solution corresponding to the surface plasmon resonance (SPR) obtained in a visible range at 439.29 nm by UV-Vis spectroscopy. FIG. 2 shows the particle size distribution by intensity obtained using a Zeta sizer, showing the average silver nanoparticle size of 43.8 nm. FIG. 3A is a photomicrograph of the Transmission Electron Microscopy (TEM) image at 150000× magnification of the silver nanoparticles. FIG. 3B is a photomicrograph of the Transmission Electron Microscopy (TEM) image at 300000× magnification of the silver nanoparticles. The shapes of the nanoparticles typically appear as spherical and elongated spherical. However, the nanoparticle is not limited to spherical shapes, but can possess various shapes, such as rods and faceted shapes etc.

Example 2

Treatment of Sewage Water by Silver Nanoparticles Synthesized by (*Trigonella foenum-graecum*) Seeds Extract About 5 ml of silver nanoparticles synthesized as described in Example 1 was added to a bottle, which contains 3 Liters of typical sewage water. Then the bottle was kept aside for 2 or 3 days, after which time the treated water was filtered. Table 1 shows the results of the concentration of chemicals treated with the silver (Ag) nanoparticles.

TABLE 1

Chemical characteristics of water treated with silver nanoparticles

| Sample | pH | EC* (ppm) | $SO_4^{2-}$ (ppm) | $Cl^-$ (ppm) | $HCO_3^-$ (ppm) | $Mg^{2+}$ (ppm) | $Ca^{2+}$ (ppm) |
|---|---|---|---|---|---|---|---|
| Normal water | 7.93 | 697.6 | 48.3 | 76.1 | 64.1 | 29.6 | 82.6 |
| Sewage Water | 8.67 | 1267.2 | 167.6 | 553.8 | 57.1 | 81.1 | 136.1 |
| Sewage water treated by Silver nanoparticles | 7.28 | 723.2 | 47.2 | 182.1 | 66.3 | 47.6 | 104.5 |

*EC = Electrical Conductivity

Example 3

Antibacterial Activity of the Silver Nanoparticles

A pure culture of *Escherichia coli* bacteria was used for assessing the antibacterial activity of the silver nanoparticles synthesized as described in Example 1. The antibacterial activities of the nanoparticles were carried out by a disc diffusion method. Nutrient agar medium plates were prepared, sterilized and solidified. After solidification bacterial cultures were swabbed on these plates. The sterile discs were dipped in nanoparticles solution of 1, 5, 10 (µg/ml) and placed in the nutrient agar plate and kept for incubation at 370° C. for 24 hours. A zone of clearing around the wells was observed, indicating the inhibitory activity of silver nanoparticles.

Example 4

Green Synthesis of Zinc Oxide (ZnO) Nanoparticles

About 15 mg of (*Trigonella foenum-graecum*) plant seeds was soaked in 30 ml distilled water over night, filtered and the aqueous extract was set aside until used. Next, 0.1 mol/ml or 6 g of zinc acetate (Merck, 99% purity) was dissolved in 50 ml boiling (*Trigonella foenum-graecum*) seeds extract and stirred continuously, allowing the extract to reduce the zinc acetate until the color changed to a deep yellow-greenish colored paste. Then the paste was dried to obtain a yellow powder of zinc oxide (ZnO) nanoparticles.

Figure 4:
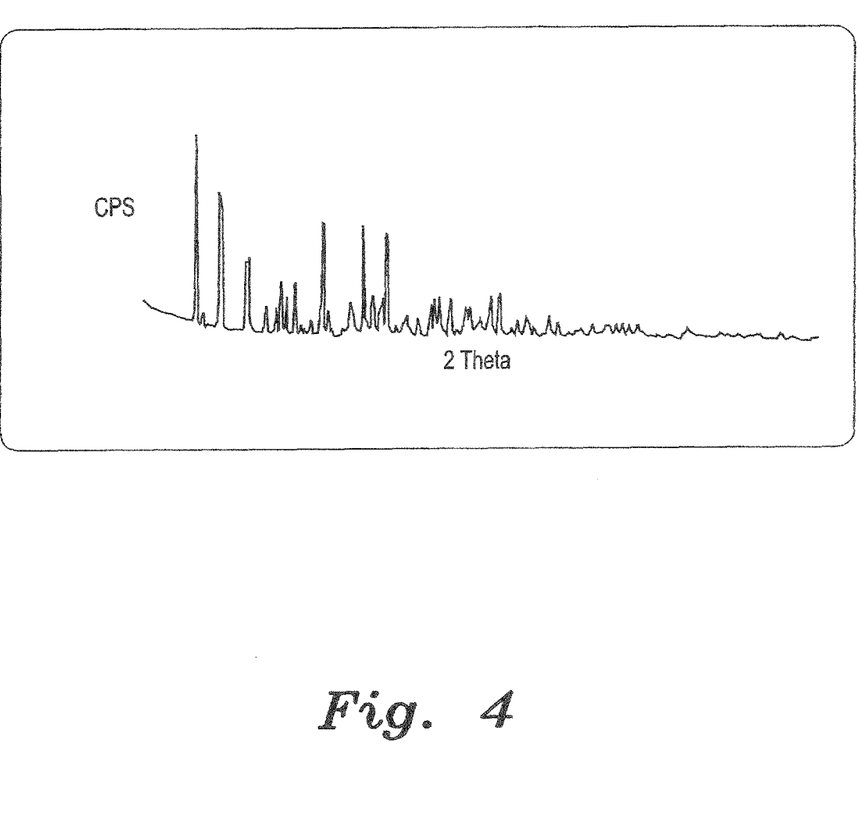
FIG. 4 is the X-ray diffraction (XRD) spectrum of zinc oxide (ZnO) nanoparticles synthesized using plant seeds extract according to the present invention.
Figure 5:
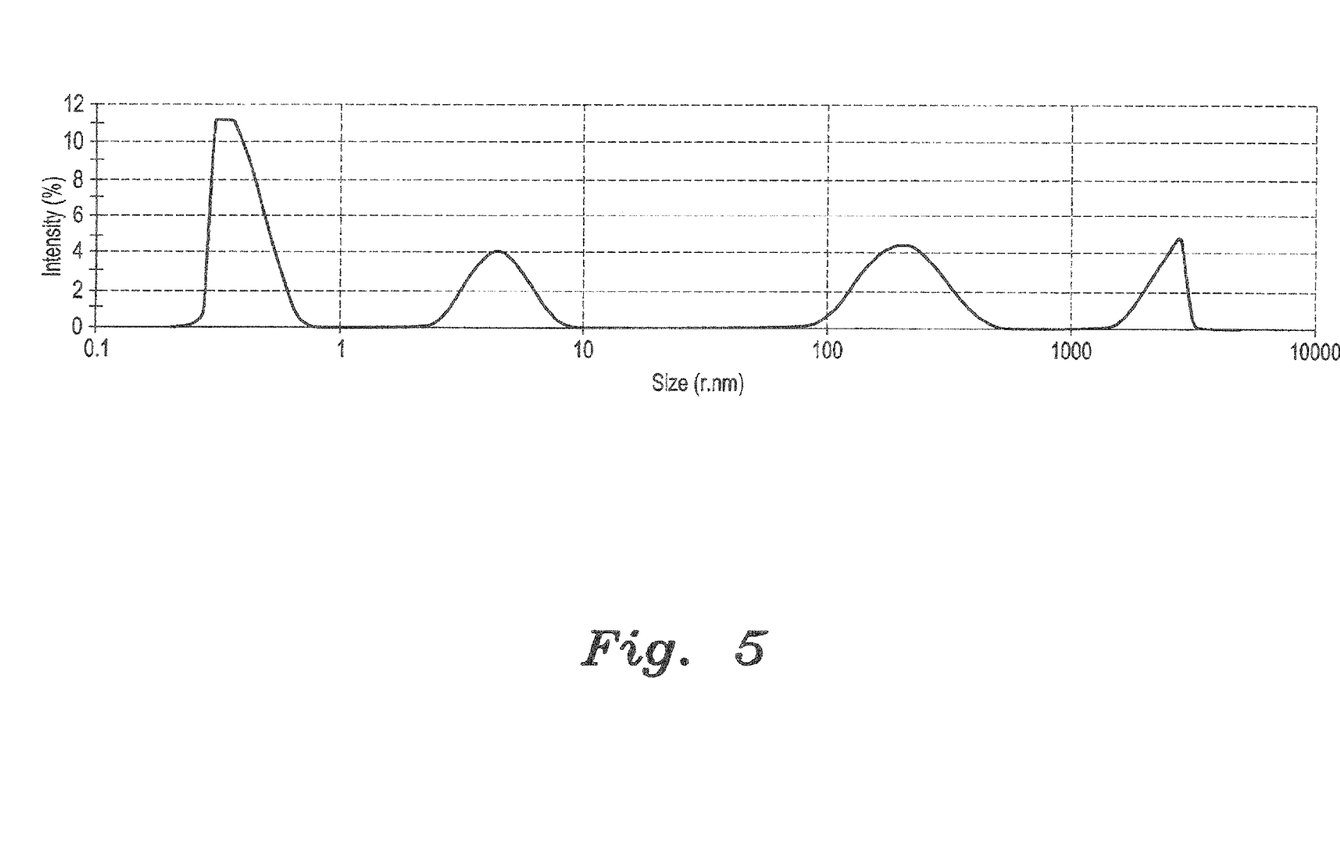
FIG. 5 is a Zita sizer chart showing the size distribution of zinc oxide nanoparticles synthesized using plant seeds extract according to the present invention.
Figure 6A:
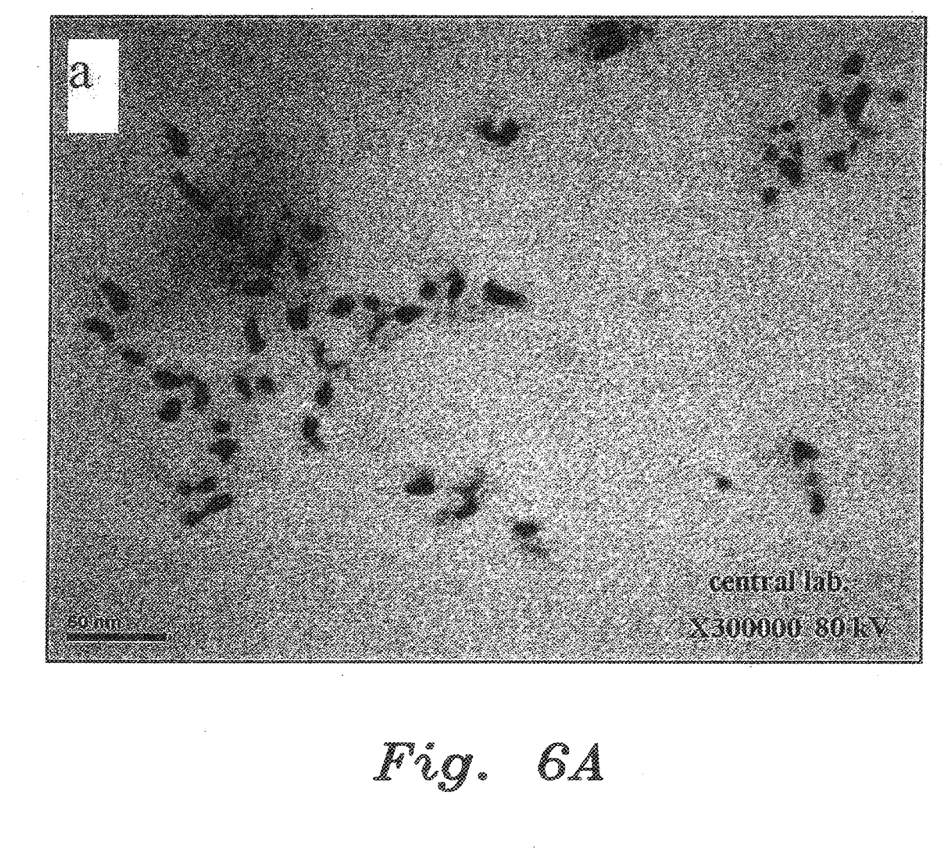
FIG. 6A is a Transmission Electron Microscopy (TEM) micrograph of zinc oxide nanoparticles synthesized using plant seeds extract according to the present invention at 300000× magnification.
Figure 6B:
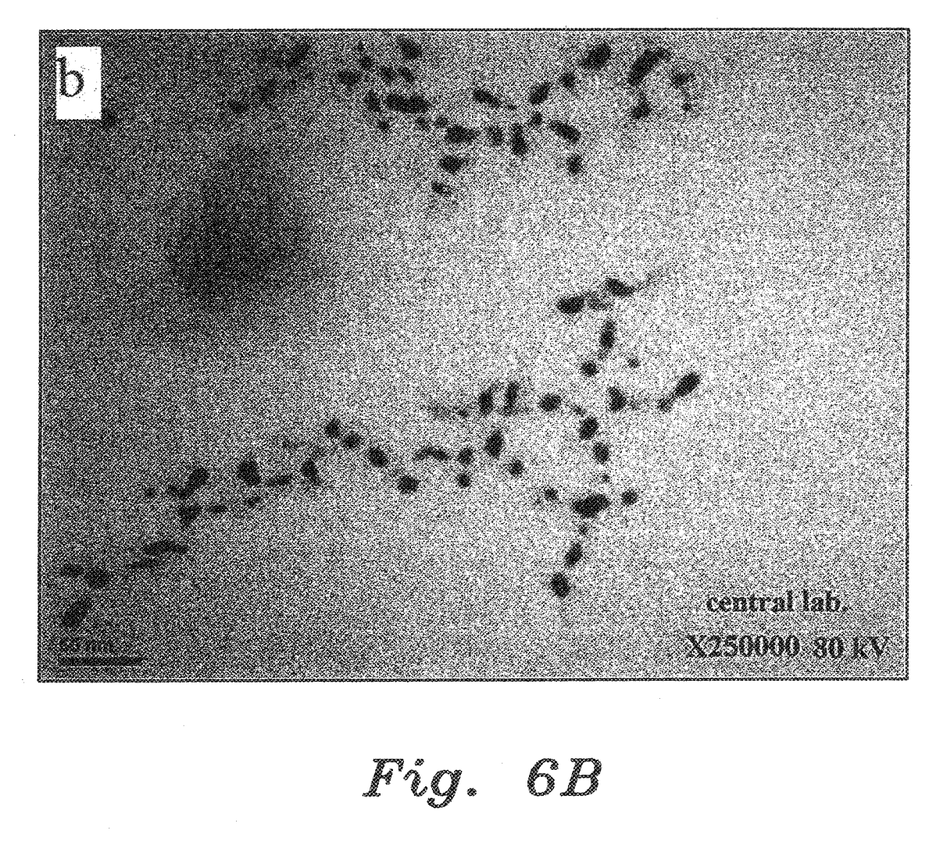
FIG. 6B is a Transmission Electron Microscopy (TEM) micrograph of zinc oxide nanoparticles synthesized using plant seeds extract according to the present invention at (250000×) magnification.

In an alternative embodiment, a few drops of 1 M of sodium hydroxide (NaOH) were added to the boiling solution until a colored paste appeared. The paste was then dried in an oven at 125° C., then the yellow powder was collected, which contained the zinc oxide nanoparticles. The formed nanoparticles were analyzed by X-ray powder diffraction (XRD) as shown in FIG. 4. FIG. 5 shows the measurement of the average particle size of 81 nm using a Zeta sizer.

Example 5

Treatment of Sewage Water by Zinc Oxide Nanoparticles Synthesized by (*Trigonella foenum-graecum*) Seeds Extract About 3 mg of zinc oxide (ZnO) nanoparticle powder synthesized as described in Example 4 was added to a glass bottle, which contained 3 L of the sewage water. The nanoparticle powder was kept aside for about 2 or 3 days, after which time, the treated water was filtered. Treatment of sewage water by zinc oxide nanoparticle synthesized by the extract of (*Trigonella foenum-graecum*) seeds was tested. The results of the chemical characteristic for the treated water are shown in Table 2.

TABLE 2

Chemical characteristics of water treated with ZnO nanoparticles

| Sample | pH | EC (ppm) | $SO_4^{2-}$ (ppm) | $Cl^-$ (ppm) | HCO (ppm) | $Mg^{2+}$ (ppm) | $Ca^{2+}$ (ppm) |
|---|---|---|---|---|---|---|---|
| Normal water | 7.93 | 697.6 | 48.3 | 76.1 | 64.1 | 29.6 | 82.6 |
| Sewage Water | 8.67 | 1267.2 | 167.6 | 553.8 | 57.1 | 81.1 | 136.1 |
| Sewage Water treated by ZnO nanoparticles | 7.28 | 723.2 | ~0 | 118.9 | 1420.5 | 74.3 | 417.1 |

*EC = Electrical Conductivity

TABLE 3

Comparison of Silver and ZnO nanoparticles on the sewage treatment

| | Raw sewage water 1 | Raw sewage water 2 | Water Sample 1 Treated with silver nanoparticles | Water Sample 2 Treated with silver nanoparticles | Water Sample 1 Treated with zinc oxide nanoparticles | Water Sample 2 Treated with zinc oxide nanoparticles |
|---|---|---|---|---|---|---|
| C.O.D* | 0.8 mg/L | 1134 mg/L | 48.3 mg/L | 262 mg/L | 120 mg/L | 990 mg/L |
| B.O.D** | Nil/0 mg/L | 807 mg/L | 21.7 mg/L | 122 mg/L | 157 mg/L | 445 mg/L |

*COD chemical oxygen demand
**BOD biochemical oxygen demand

Example 6

Green Synthesis of Gold (Au) Nanoparticles

Figure 7:
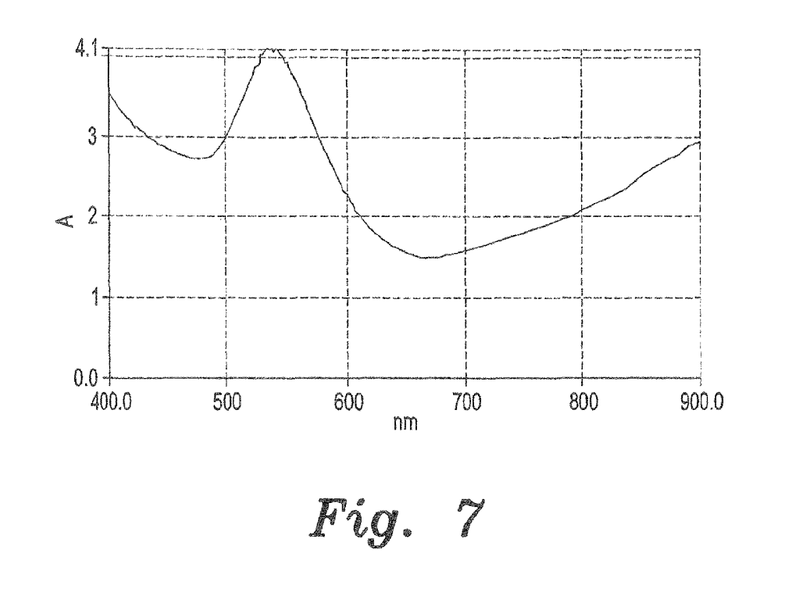
FIG. 7 is the UV-Vis spectrum of gold (Au) nanoparticles synthesized using plant seeds extract according to the present invention.
Figure 8:
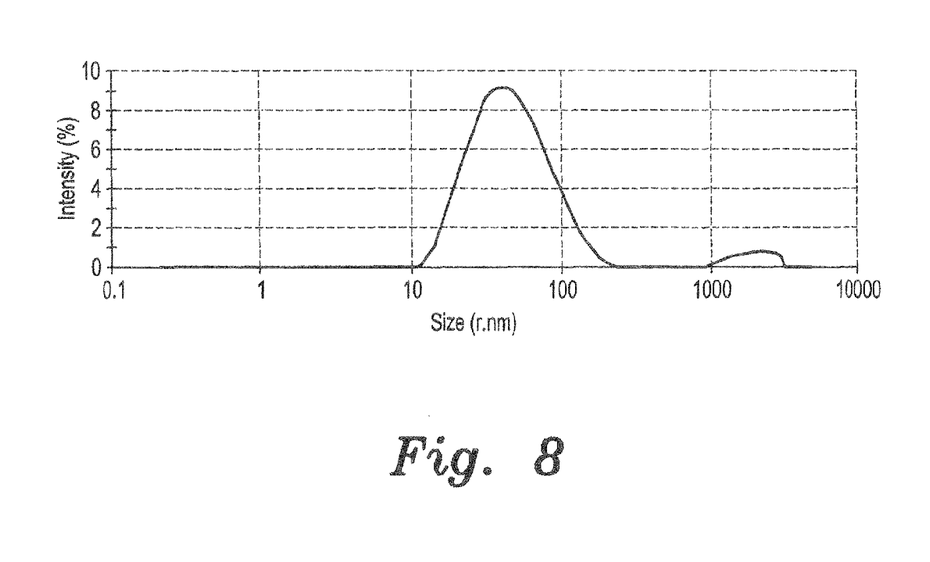
FIG. 8 is a Zita sizer chart showing the size distribution of gold (Au) nanoparticles synthesized using plant seeds extract according to the present invention.
Figure 9A:
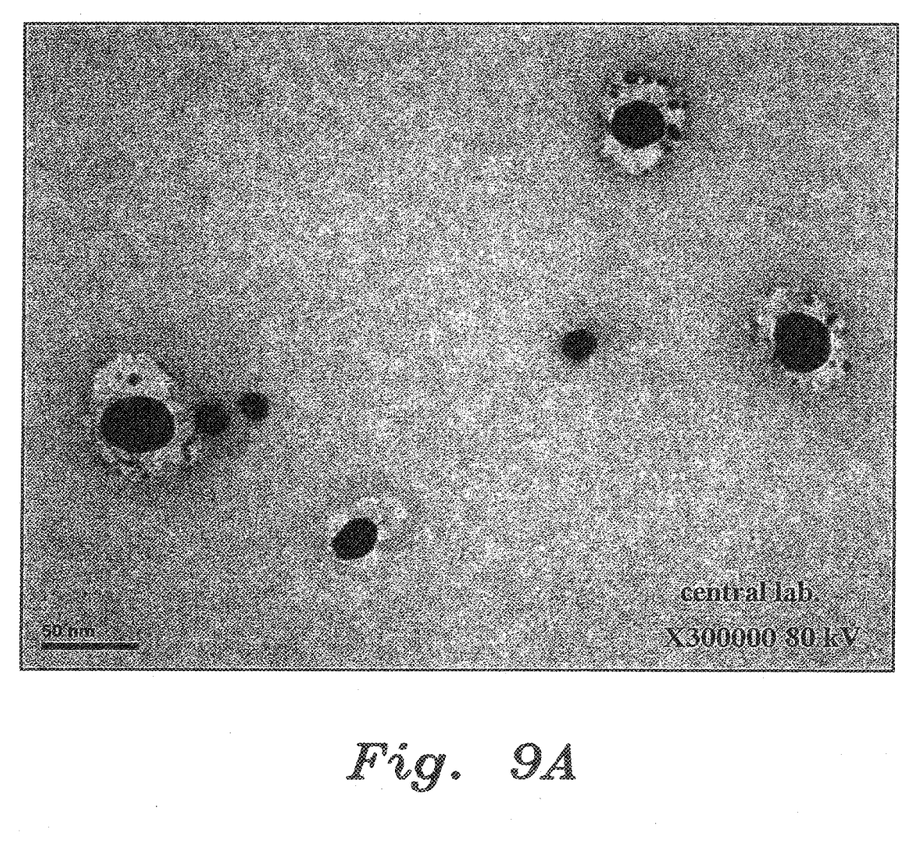
FIG. 9A is a Transmission Electron Microscopy (TEM) micrograph of gold nanoparticles synthesized using plant seeds extract according to the present invention at 300000× magnification.
Figure 9B:
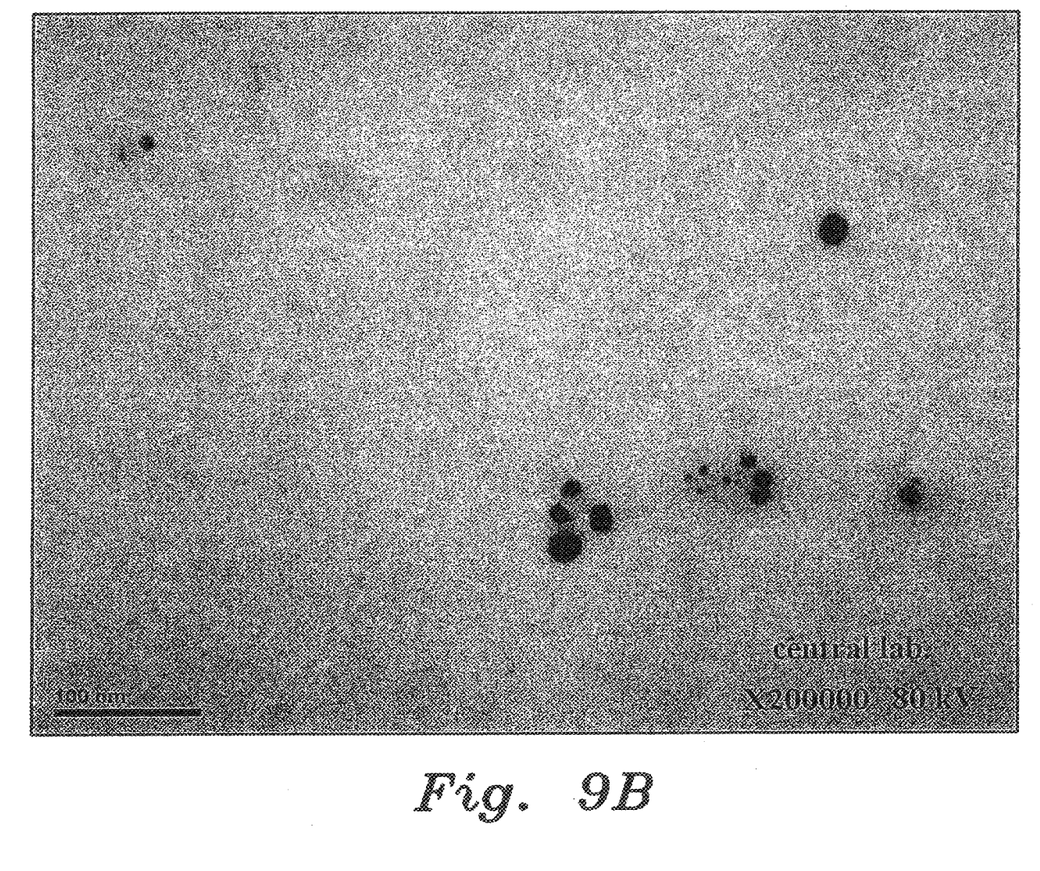
FIG. 9B is a Transmission Electron Microscopy (TEM) micrograph of gold nanoparticles synthesized using plant seeds extract according to the present invention at 200000× magnification.
Figure 10:
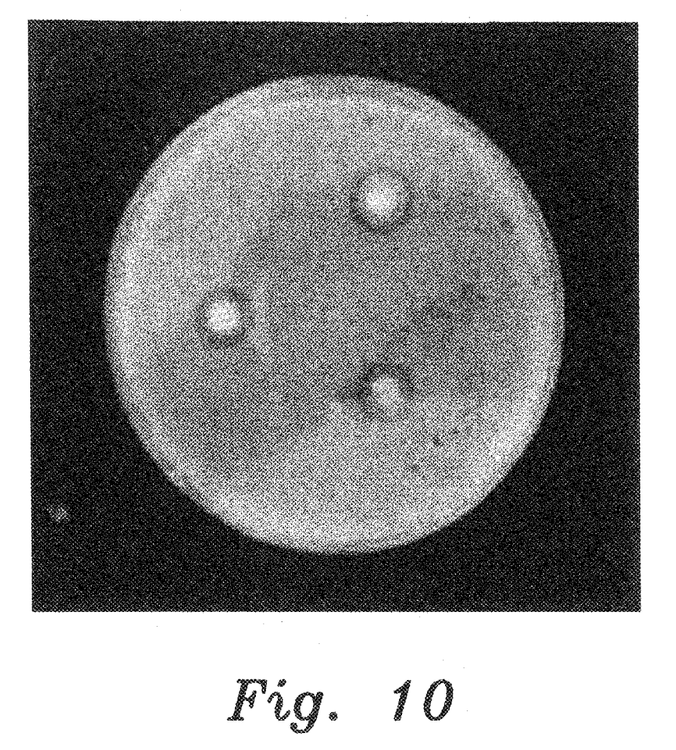
FIG. 10 shows the antibacterial assay against *E. Coli* of green silver nanoparticles synthesized according to the present invention.
Figure 11:
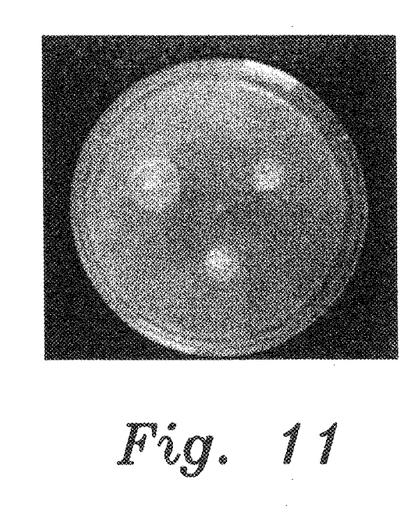
FIG. 11 shows the antibacterial assay against *E. Coli* of green Zinc Oxide (ZnO) nanoparticles synthesized according to the present invention.

About 15 mg of (*Trigonella foenum-graecum*) plant seeds was soaked in 30 ml distilled water overnight, then filtered and the aqueous extract was set aside until used. Next, 5 ml of the aqueous extract was added to about 50 ml of an aqueous solution of 1 mmol/ml Chloroauric Acid ($HAuCl_4$) and stirred for about 15 minutes at 45° C. The synthesis of gold nanoparticles due to the reduction by the seeds extract was monitored by a color change from colorless solution to dark red. The formed nanoparticles were analyzed with UV-Vis spectroscopy. FIG. 7 shows the absorption peak at 538.97 nm corresponding to the surface plasmon resonance (SPR) of gold nanoparticles obtained in a visible range at by UV-Vis spectroscopy. FIG. 8 shows a graph of the intensity versus particle size measured by Zita sizer. The average particle size diameter was found to be 35.7 nm. FIGS. 9A and 9B are photomicrographs of the Transmission Electron Microscopy (TEM) image of biologically synthesized gold nanoparticles according to this example. The images show spherical and elongated spherical shapes of the gold nanoparticles.

The above examples demonstrate the aqueous extract of *Trigonella foenum-graecum* seeds is capable of producing silver, gold and zinc oxide nanoparticles. Additionally, the "green" nanoparticles show their effectiveness in the treatment of sewage water in reducing contaminants and as antibacterial agent. Nanomaterials produced by the "green" synthesis reveal good result than other techniques used in water treatment because of its high surface area (surface/volume ratio). Silver nanomaterials reveal better results than other techniques used in water treatment because of its high surface area (surface/volume ratio). It is suggested that these may be used in future at large scale water purification. It is also found that the coliform bacteria treated with ultrasonic irradiation for short time period before Ag nanoparticle treatment at low concentration, enhanced antibacterial effect. In future, a combination of both may be the best option for treatment of waste and sewage water.

Moreover, the metal and metal oxide nanoparticles prepared according to the above examples possess various applications, e.g., in medical diagnostic tests, incorporation into healing aid bandages, targeted drug delivery vehicles, chemical synthesis systems, pollution control or monitoring devices, fuel cells, an electronic devices, as anti-microbial agents in wound or burn areas with respect to an antibiotic-resistant genotype in said wound or burn area, anti-cancer and/or tumor vaccines and/or antibacterial drug delivery and cosmetic agent. It is also found that the coliform bacteria treated with ultrasonic irradiation for short time period before Ag nanoparticle treatment at low concentration enhanced antibacterial effect. Success of the rapid and ecofriendly green method for synthesizing metallic nanoparticle is an alternative to chemical synthesis methods.

It is to be understood that the present invention is not limited to the embodiments described above, but encompasses any and all embodiments within the scope of the following claims.

We claim:

1. A method of synthesizing zinc oxide nanoparticles, comprising the steps of:
   providing a solution of zinc ions;
   providing plant seeds extract solution and
   combining the zinc ion solution and the plant extract solution while stirring at a temperature of 40° C. to 100° C. to produce the zinc oxide nanoparticles
   wherein the plant extract is obtained from the seeds of *Trigonella foenum-graecum* plant.

2. The method of synthesizing zinc oxide nanoparticles according to claim 1, wherein the combined zinc ion and plant extract solution is heated and stirred at a temperature of 100° C.

3. The method of synthesizing zinc oxide nanoparticles according to claim 1, further comprising the step of adding sodium hydroxide (1 M) into the solution.

4. The method of synthesizing zinc oxide nanoparticles according to claim 1, wherein said zinc oxide nanoparticles have a mean diameter in the range from about 20 to about 200 nm.

5. The method of synthesizing zinc oxide nanopaxticles according to claim 1, wherein said zinc oxide nanoparticles have shapes selected from the group consisting of spherical, spheroidal, elongated spherical, rod and faceted shape.

* * * * *